(12) United States Patent
Luo et al.

(10) Patent No.: US 8,391,966 B2
(45) Date of Patent: Mar. 5, 2013

(54) SENSORY-EVOKED POTENTIAL (SEP) CLASSIFICATION/DETECTION IN THE TIME DOMAIN

(75) Inventors: An Luo, San Jose, CA (US); Thomas J. Sullivan, San Jose, CA (US); Arnaud Delorme, San Diego, CA (US)

(73) Assignee: NeuroSky, Inc., San Jose, CA (US)

( * ) Notice: Subject to any disclaimer, the term of this patent is extended or adjusted under 35 U.S.C. 154(b) by 0 days.

(21) Appl. No.: 12/886,140

(22) Filed: Sep. 20, 2010

(65) Prior Publication Data

US 2011/0040202 A1 Feb. 17, 2011

Related U.S. Application Data

(63) Continuation-in-part of application No. 12/381,887, filed on Mar. 16, 2009, now Pat. No. 8,155,736.

(60) Provisional application No. 61/250,263, filed on Oct. 9, 2009.

(51) Int. Cl.
*A61B 5/04* (2006.01)
*A61B 5/05* (2006.01)

(52) U.S. Cl. .......... 600/544; 607/45; 600/545; 600/372; 600/509; 600/546; 600/547

(58) Field of Classification Search .......... 600/544–547, 600/372, 509; 607/45
See application file for complete search history.

(56) References Cited

U.S. PATENT DOCUMENTS

| | | | |
|---|---|---|---|
| 4,421,122 A | 12/1983 | Duffy | |
| 4,493,327 A | 1/1985 | Bergelson et al. | |
| 4,800,888 A * | 1/1989 | Itil et al. | 600/383 |
| 4,926,969 A | 5/1990 | Wright et al. | |
| 5,447,166 A * | 9/1995 | Gevins | 600/544 |
| 5,495,853 A | 3/1996 | Yasushi | |
| 5,687,291 A * | 11/1997 | Smyth | 706/10 |
| 5,813,993 A * | 9/1998 | Kaplan et al. | 600/544 |
| 6,001,065 A | 12/1999 | DeVito | |
| 6,033,073 A | 3/2000 | Potapova et al. | |
| 6,231,187 B1 | 5/2001 | Munoz et al. | |
| 6,254,536 B1 | 7/2001 | DeVito | |
| 6,296,543 B1 | 10/2001 | Andrews | |
| 6,317,627 B1 | 11/2001 | Ennen et al. | |
| 6,602,202 B2 | 8/2003 | John et al. | |
| 7,123,955 B1 | 10/2006 | Gao et al. | |
| 7,260,430 B2 * | 8/2007 | Wu et al. | 600/545 |
| 7,392,079 B2 | 6/2008 | Donoghue et al. | |
| 7,751,877 B2 * | 7/2010 | Flaherty et al. | 600/544 |

(Continued)

OTHER PUBLICATIONS

Middendorf et al., "Brain-Computer Interfaces Based on the Steady-State Visual-Evoked Response", IEEE Transactions on Rehabilitation Engineering, vol. 8, No. 2, pp. 211-214, Jun. 2000. *Summarizes results from Air Force Research Lab. Uses lock-in amplifier technique.

(Continued)

*Primary Examiner* — Navin Natnithithadha
*Assistant Examiner* — Sunita Reddy
(74) *Attorney, Agent, or Firm* — Van Pelt, Yi & James LLP

(57) ABSTRACT

Techniques are disclosed for sensory-evoked potential (SEPs, e.g., visual-evoked potentials) signal detection/classification by synchronizing EEG to the repeated presentation of sensory stimuli in the time domain. In some embodiments, a system receives a plurality of EEG signal samples, generates a stimulus-locked EEG and determines whether the plurality of EEG signal samples are evoked in response to a pattern of stimulus. In some embodiments, no prior knowledge about the update pattern (such as the flashing frequency of a visual stimulus) of the stimulus and no prior knowledge about an individual user's EEG pattern are required.

16 Claims, 18 Drawing Sheets

U.S. PATENT DOCUMENTS

| | | | |
|---|---|---|---|
| 2003/0176806 A1* | 9/2003 | Pineda et al. | 600/544 |
| 2003/0225340 A1 | 12/2003 | Collura | |
| 2003/0225342 A1 | 12/2003 | Hong et al. | |
| 2004/0097824 A1 | 5/2004 | Kageyama | |
| 2004/0249302 A1* | 12/2004 | Donoghue et al. | 600/544 |
| 2005/0017870 A1 | 1/2005 | Allison et al. | |
| 2005/0085744 A1* | 4/2005 | Beverina et al. | 600/558 |
| 2005/0131311 A1 | 6/2005 | Leuthardt et al. | |
| 2005/0203366 A1* | 9/2005 | Donoghue et al. | 600/378 |
| 2005/0273890 A1* | 12/2005 | Flaherty et al. | 901/50 |
| 2005/0283053 A1* | 12/2005 | deCharms | 600/300 |
| 2006/0129277 A1 | 6/2006 | Wu et al. | |
| 2006/0293578 A1* | 12/2006 | Rennaker, II | 600/378 |
| 2007/0066914 A1 | 3/2007 | Le et al. | |
| 2007/0173733 A1 | 7/2007 | Le et al. | |
| 2008/0208072 A1* | 8/2008 | Fadem et al. | 600/544 |
| 2009/0062676 A1 | 3/2009 | Kruglikov et al. | |
| 2009/0076462 A1 | 3/2009 | Kiani | |
| 2009/0326404 A1* | 12/2009 | Sajda et al. | 600/544 |
| 2010/0109859 A1 | 5/2010 | Lakosky | |
| 2010/0185113 A1* | 7/2010 | Peot et al. | 600/544 |
| 2011/0289030 A1 | 11/2011 | Lu et al. | |

OTHER PUBLICATIONS

Burkitt et al., "Steady-state visual evoked potentials and travelling waves", Clinical Neurophysiology, vol. 111, pp. 246-258, Jul. 18, 1999. *Analyses phase topography of SSVEP.

Pastor et al., "Human cerebral activation during steady state visual-evoked responses", The Journal of Neuroscience, vol. 23, No. 37, pp. 11621-11627, Dec. 17, 2003. *Frequency and topography of EEG response to SSVEP signals.

Muller-Putz et al., "Steady-state visual evoked potential (SSVEP)-based communication: impact of harmonic frequency components", Journal of Neural Engineering, vol. 2, pp. 123-130, Sep. 28, 2005. *Uses harmonics of SSVEP signal to increase classification rate.

Mukesh et al., "A novel multiple frequency stimulation method for steady state VEP based brain computer interfaces", Physiological Measurement, vol. 27, pp. 61-71, Dec. 1, 2005.

Wang et al., "A Practical VEP-Based Brain-Computer Interface", IEEE Transactions on Neural Systems and Rehabilitation Engineering, vol. 14, No. 2, pp. 234-239, Jun. 2006.

Sullivan et al., "A Low-Noise, Non-Contact EEG Sensor", Biomedical Circuits and Systems Conference, 2007.

Muller-Putz et al., Comparison of DFT and Lock-In Amplifier Features and Search for Optimal Electrode Positions in SSVEP-based BCI, Jun. 20, 2007.

Fisher et al., Photic-and Pattern-induced Seizures: A Review for the Epilepsy Foundation of America Working Group, May 26, 2005.

Martinez et al., "Fully OnlineMulticommand Brain-Computer Interface with Visual Neurofeedback Using SSVEP Paradigm", Computational Intelligence and Neuroscience, vol. 2007, Article ID 94561, May 22, 2007. *Car game. AMUSE BSS, Band-pass filters, Savitzky-Golay filters, ANFIS classifier.

Fukuda et al., "Pattern Classification of Time-series EEG Signals Using Neural Networks", Robert and Human Communication, 5th IEEE International Workshop on, pp. 217-222, 1996.

Kaplan et al., Application of the Change-Point Analysis to the Investigation of the Brains's Electrical Activity, Chapter 7 in Brodsky et al., Nonparametric Statistical Diagnosis: Problems and Methods, pp. 333-388, 2000.

Borisov et al., Analysis of EEG Structural Synchrony in Adolescents with Schizophrenic Disorders, Jun. 7, 2004.

A. Kaplan, The Problem of Segmental Description of Human Electoencephalogram, Mar. 18, 1998.

Landa et al., A Model for the Speed of Memory Retieval, Published Oct. 21, 2003.

Levichkina et al., Unconscious Context Control of Visual Perception of Simple Stimuli: A Study Using Evoked Potentials, Aug. 2, 2007.

Kaplan et al., Unconscious Operant Conditioning in the Paradigm of Brain-Computer Interface Based on Color Perception, Jun. 29, 2004.

Kaplan et al., Macrostructural EEG Characterization Bases on NonParametric Change Point Segmentation: Application to Sleep Analysis, Jan. 8, 2001.

Shishkin et al., Combining the Extremities on the Basis of Separation: A New Approach to EEG/ERP Source Localization, Nov. 2004.

* cited by examiner

LEDs 650

LEDs 650

SENSORY-EVOKED POTENTIAL (SEP) CLASSIFICATION/DETECTION IN THE TIME DOMAIN

CROSS REFERENCE TO OTHER APPLICATIONS

This application is a continuation in part of U.S. patent application Ser. No. 12/381,887 entitled EEG CONTROL OF DEVICES USING SENSORY EVOKED POTENTIALS, filed Mar. 16, 2009, which is incorporated herein by reference for all purposes; and this application claims priority to U.S. Provisional Patent Application No. 61/250,263 entitled SENSORY-EVOKED POTENTIAL (SEP) CLASSIFICATION/ DETECTION IN THE TIME DOMAIN filed Oct. 9, 2009, which is incorporated herein by reference for all purposes.

BACKGROUND OF THE INVENTION

EEG detection systems exist that include bio-signal sensors (e.g., electroencephalography (EEG) sensors) that allow brain waves of a user to be measured. Sensory Evoked Potentials (SEPs) are generally involuntary EEG signals of a person generated when the person responds to a stimulus (e.g., visually-evoked potentials, or EEG potentials evoked through other senses, such as tactile-evoked or audio-evoked potential). Thus, it is desirable to provide EEG detection systems that can be used for SEP applications and/or EEG control of devices using SEPs, such as visually-evoked potentials.

BRIEF DESCRIPTION OF THE DRAWINGS

Various embodiments of the invention are disclosed in the following detailed description and the accompanying drawings.

DETAILED DESCRIPTION

Figure 1:
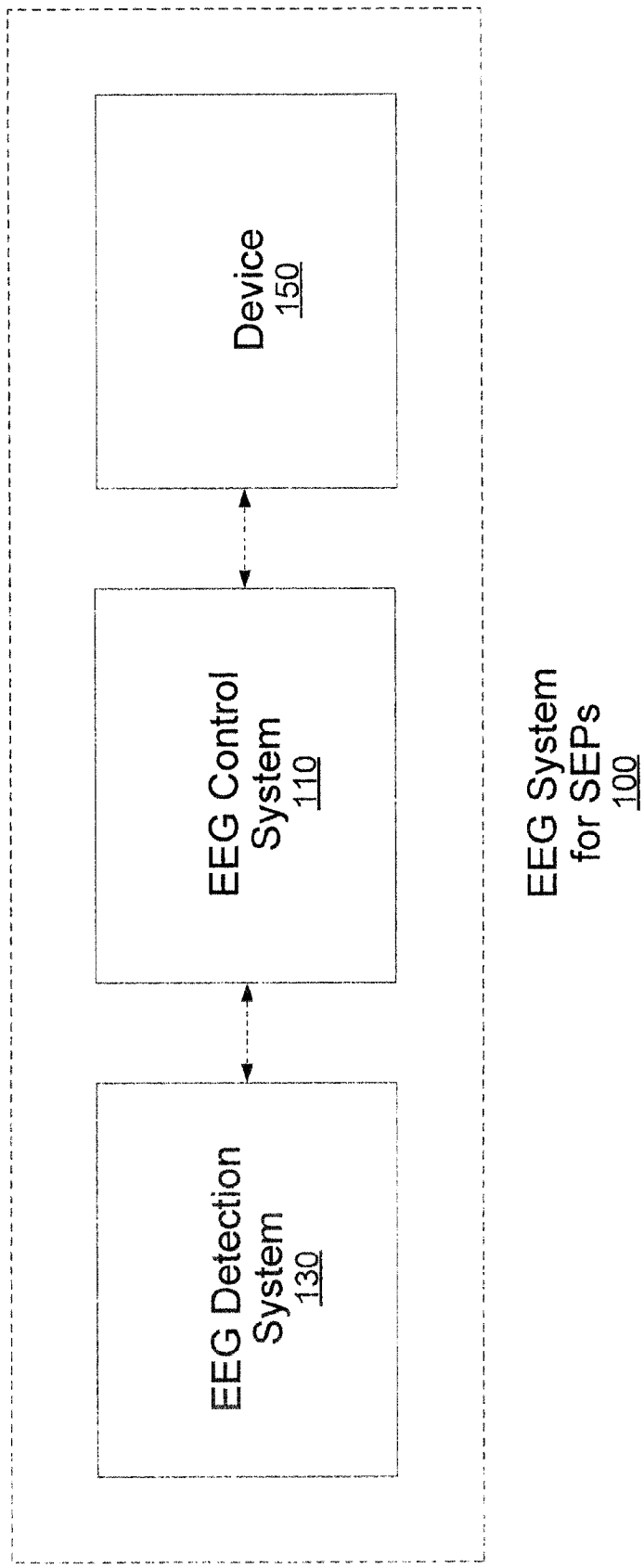
FIG. 1 is a block diagram illustrating an EEG system for SEPs in accordance with some embodiments.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits (e.g., PCBs, ASICs, and/or FPGAs), and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

The typical electroencephalography (EEG) signal that is generated from a stimulus event, such as the user looking at a flashing light, is a relatively weak signal. As a result, it is not easy to detect such signals with the typical amount of noise (e.g., from the circuit, external sources, and/or non-relevant EEG sources) in the detected signal (e.g., using dry, contact sensor(s), wet, contact sensor(s), or non-contact EEG sensor(s)). In addition, it is also not easy to detect the signature EEG signal in a timely manner (e.g., within 2 to 3 seconds). For example, systems that use lights that flash at fixed frequencies rely on monitoring EEG signals for an increase in power at the light frequencies. These systems and methods are generally referred to as steady-state visually-evoked potentials (SS-VEPs). However, power estimation techniques (e.g., FFT techniques) are not reliable when the level of noise in the EEG signal is of the same order as the signal that is being estimated, which is often the case, especially with non-contact EEG sensors.

Techniques that rely on EEG potentials generated by thoughts or high-level perceptions are slow. For example, with P300 event-related potentials (ERPs), the user must recognize relatively rare events requiring that events be spaced relatively far apart in time (e.g., ten events will be spaced over one minute), which limits the speed at which a determination/action can be performed with EEG-based control.

So far most SEP classification algorithms are developed in the frequency domain. For example, many have used discrete Fourier transform (DFT) to extract features for classification. However, frequency-domain-based algorithms have limitations. For example, when the update frequency of the stimulus cannot be an exact predefined value or it varies across devices, a more flexible method which does not depend on prior knowledge about the update frequency of the stimulus is required. It is also worth noting that when VEP is elicited by stimulus with irregular patterns, a frequency-domain-based method is likely to fail.

Accordingly, a system and method that can efficiently and effectively determine stimulus-evoked events (e.g., SEPs, such as visually-evoked potentials) based on EEG signals is needed. Moreover, it is desirable to develop a technique that does not require prior knowledge about the update pattern of the stimulus or prior knowledge about EEG in response to SEP (e.g., the technique still works even when the stimulus changes or when a different user is using it).

In some embodiments, a system is provided that efficiently and effectively identifies EEG signals associated with SEPs to control a device. In some embodiments, a system is provided that uses flashing lights (e.g., from one or more light-emitting diodes (LEDs) and/or from a computer screen or television (TV) screen) that correspond to commands to/from a user. In some embodiments, the flashing lights in the system flash at distinct fixed frequencies. In some embodiments, the flashing lights in the system flash at variable frequencies in a fixed pattern or in non-periodic frequencies. The system records detected EEG signals of the user and determines whether/when a user is looking at one of the flashing lights. As used herein, SEPs generally refer to involuntary EEG signals generated when the user is exposed to (e.g., rapidly) repeating sensory stimuli (e.g., visual, such as a flashing light or another involuntary response to a visual stimulus event, audio, tactile, or other stimulus event). As used herein, SEPs do not include events based on a user's thought and higher level perceptions (e.g., recognition of a relatively rare event, like P300s, or recognition of a grammar mistake), which generally occur after a longer period of time offset (and generally require a relatively slow repetition of such events so that the small EEG signal samples can be added and averaged for identification purposes), and which are generally referred to as event-related potentials (ERPs).

In some embodiments, an EEG segment refers to one or multiple EEG samples that were recorded from one time point to a later time point. In some embodiments, an EEG segment can have variable length and two successive EEG segments may or may not overlap with each other.

Figure 18:
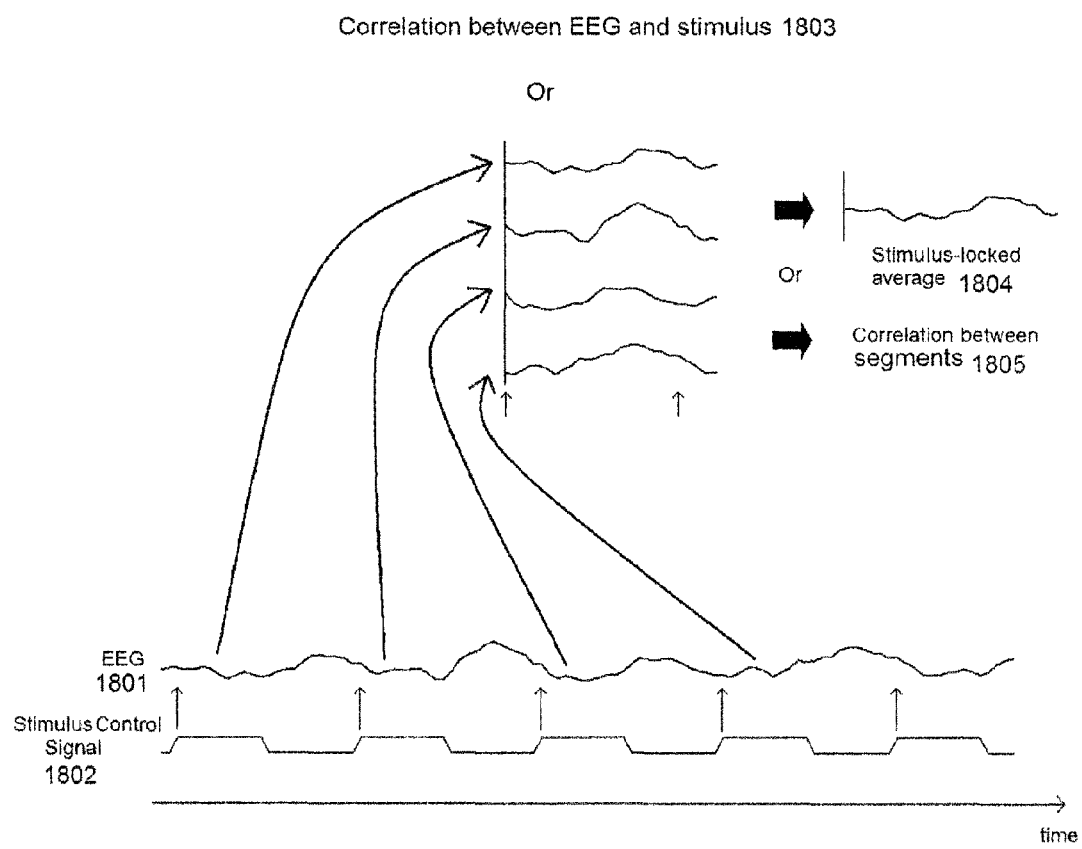
FIG. 18 is a chart illustrating an example for generating a stimulus-locked signal in accordance with some embodiments.

In some embodiments, a system is provided that uses various signal analysis techniques on SEP signals generated in response to rapidly repeating sensory stimuli. In some embodiments, such as shown in FIG. 18, an EEG signal 1801 from a user reacting to a rapidly repeated stimulus event, such as the user looking at a flashing light, and a signal 1802 that is used to control the stimulus are both measured. For example, segments of the EEG signal of a fixed length (e.g., 500 milliseconds (ms)) that follow the light onsets are first recorded. The recorded data is then averaged together such that the first EEG data points following stimulus onsets are averaged together, then all the second data points that follow stimulus onsets are averaged together, then the third data points that follow stimulus onsets are averaged together, and so forth. The result provides a stimulus-locked average signal (or in this example, a flash-locked average signal). In some embodiments, this average signal can have the same length as the time interval between the two light onsets, or is longer or shorter than this interval. The signal is averaged across recorded segments; therefore, the average signal will have the same length as the recorded segments. For example, if the user looked at a light, then the averaged waveform will include a characteristic shape (e.g., a positive deflection in EEG voltage about 30 ms after the light onset time). This characteristic shape of the averaged waveform can be detected in a variety of ways as further described herein. If the user did not look at the light the averaged waveform will be mostly flat.

In some embodiments, a stimulus-locked sum, variance or median signal, or any computation that represents some statistical aspect of the stimulus-locked EEG signal, can be obtained in a similar way. This signal may have the same length as the time interval between the two stimulus onsets, or is longer or shorter than this interval. If the user is attending to a stimulus, this signal will include a characteristic shape which can be detected in a variety of ways.

Figure 17:
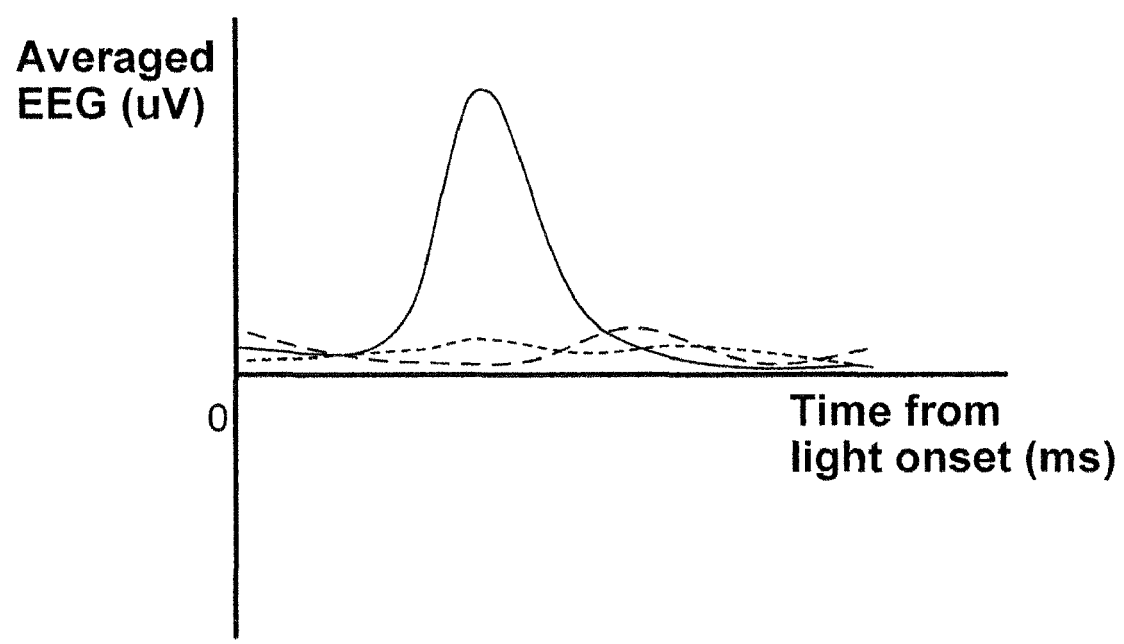
FIG. 17 is a chart illustrating an example of four stimulus-locked averages in accordance with some embodiments.

In some embodiments, the system includes more than one stimuli. For example, FIG. 17 is a chart illustrating an example of four stimulus-locked averages. One of the averages has developed a characteristic shape, whereas, the other averages are relatively flat.

The characteristic shape of the above mentioned stimulus-locked signal can be detected using various techniques including comparing to a threshold at some delay from the onset, integrating the stimulus-locked average (or sum, median, variance, etc) signal over some time period and comparing that result to a threshold, or creating a classifier that distinguishes if the light is being attended. As another example, a prototype of an ideal signal (e.g., when a light is being attended) can be constructed and multiplied by the actual signal. A high value result will indicate an attended light. The prototype can be constructed in a variety of ways, including computing EEG averages (or sum, median, variance, etc.) when a user is known to be looking at the light, or constructing an auto-regression model of EEG data when a user is known to be looking at the light, and using the coefficients of that auto-regression model as the data elements of the prototype.

In some embodiments, an EEG signal from a user reacting to a rapidly repeated stimulus event, such as the user looking at a flashing light, and a signal that is used to control the stimulus are both recorded. In some embodiments, as described in FIG. 18, EEG data are first synchronized to the repeated events/status of each stimulus, and multiple segments are obtained for some period of time. The segments can be the same or shorter/longer than the time interval between two successive stimulus events.

In some embodiments, the correlation coefficient, mutual information, covariance, or any computation that measures the mutual relationship between every pair of these segments (or a subset of these segments, or a part of the segments, such as the second half of a segment, or both) is computed. Next the average/median value, and/or any measures related to the statistics of the said mutual relationship can be calculated for each stimulus. These values provide a measure of how related the EEG segments are with each other when they are synchronized to each stimulus. If the user is attending to one stimulus, the corresponding value (such as an average correlation coefficient) will be higher than the values corresponding to other stimuli.

In some embodiments, the mutual relationship, such as correlation coefficient, mutual information, covariance, or other mutual relationship, between each individual segment and the average/median/sum of the EEG segments can be computed. Next, the average, median, or any computation related to the statistics of the said mutual relationship can be calculated for each stimulus. If the user is attending to one stimulus, the corresponding computation will be higher than those corresponding to other stimuli.

In some embodiments, SEP classification/detection in the time domain includes receiving a plurality of electroencephalography signal samples; generating a stimulus-locked electroencephalography signal sample; and determining whether the plurality of electroencephalography signal samples are evoked in response to a pattern of stimulus. In some embodiments, SEP classification/detection in the time domain further includes calculating a mutual relationship between pairs of segments for the stimulus-locked electroencephalography signal sample; determining a statistical measure of the mutual relationship for each stimulus; and determining if a stimulus is being attend to by a user according to the statistic measure of the mutual relationship for each stimulus using a classifier. In some embodiments, the mutual relationship includes correlation, mutual information, or covariance. In some embodiments, the statistical measure includes a mean, a median value, or a sum. In some embodiments, the classifier is implemented as a linear discrimination analysis (LDA), neural network, or support vector machine (SVM). In some embodiments, the maximal mutual relationship value is compared to a threshold, and if it is larger than the threshold, the corresponding stimulus is likely to be attended.

In some embodiments, EEG data are first synchronized to the repeated events/status of each stimulus, and the mutual relationship, such as correlation coefficient, mutual information, covariance, or other mutual relationship, between EEG and the stimulus can be computed. If the user is attending to one stimulus the corresponding mutual relationship will be higher than those corresponding to other stimuli.

A variety of methods can be further applied to decide whether the user is attending to a stimulus and/or which stimulus the user is attending to by looking at the aforementioned mutual relationship measures. For example, a classifier, such as linear discrimination analysis (LDA) which is obtained through training of some sample data, can be built to decide whether a stimulus is being attended. Or one can compare the maximal mutual relationship value to a threshold, and if it is larger than the threshold, the corresponding stimulus is likely to be attended.

In some embodiments, the system is used to control devices using certain EEG signals that are evoked by a user looking at flashing lights. For example, a control signal can also be provided to another device (e.g., an entertainment system, an educational system, a medical system, an application for automobiles, and a computer executing an application) based on detected SEPs. For example, the system can include several flashing lights that each represents a command that is used to control the device. When a user looks at one of the flashing lights, a unique signature in the EEG signal can be determined to be present in the user's recorded EEG signals pattern using stimulus-locked average techniques. For example, a computing device (e.g., a programmed computer/laptop/netbook/portable computing device, microcontroller, ASIC, and/or FPGA) can perform an efficient and effective algorithm (e.g., classifier) that continuously checks for unique EEG signal signatures that correspond to each flashing light. In some embodiments, the algorithm performs such determinations in real-time (e.g., computes such determinations within about 3 seconds of the event, in this case, the flashing light(s) event(s)). In some embodiments, such determination are performed offline (e.g., after all data are collected). In some embodiments, various parameters are adjusted to maximize the EEG signal and increase the visually-evoked potential detection rate, such as light brightness, color, spacing, frequency, duty cycle, and the amount of visual field that is used by the lights. When a visually-evoked potential is detected, then the corresponding command is sent to the controlled device.

For example, the device that is controlled can be a toy, and when the system recognizes that one of the flashing lights is being looked at by the user, then something fun happens with the toy (e.g., based on a command from the system for detecting SEPs). As another example, objects within a video game can flash, and the game can recognize what the user is looking at (e.g., which flashing object) and incorporate that into the game play. As another example, objects within a flight simulator or a military or other application can flash, and the game can recognize what the user is looking at (e.g., which flashing object) and incorporate that into the application. As another example, the device that is controlled can be a programmed computer, or any apparatus, that allows a user who cannot use their hands, but needs the ability to make a system selection. As another example, the device that is controlled can be an automobile application, in which a selection or setting for an automobile interface for drivers and/or passengers. For example, the EEG detection system can be in the form of a cap worn by the user and/or integrated into a headrest of an automobile seat, and blinking/flashing lights can be integrated into a console/dashboard of the automobile for controlling radio, temperature, or other controls/settings, or combined with various other EEG applications for automobiles or other devices, such as a mental state monitor (e.g., for determining attention, anxiety, surprise, and/or drowsy states, such as for a driver of the automobile, an airplane, or any other device).

FIG. 1 is a block diagram illustrating an EEG system for SEPs in accordance with some embodiments. As shown, an EEG system for SEPs 100 includes an EEG control system 110, an EEG detection system 130, and a device 150. In some embodiments, the device 150 is controlled by the EEG control system 110. In some embodiments, the device 150 is included with or integrated with the EEG system for SEPs, as shown, and communicates with the device 150 using a serial or other communication channel. In some embodiments, the device 150 is separate from the EEG system for SEPs 100 and is in communication with the EEG control system 110 using a wired line or wireless communication. In some embodiments, the EEG control system 110 communicates with the EEG detection system 130 using a serial or other communication channel (e.g., wired or wireless).

In some embodiments, the EEG detection system 130 detects EEG signals of a user, and the EEG control system 110 includes a processor configured to perform an SEP determination algorithm (e.g., a real-time classification algorithm/classifier) for EEG signals detected by EEG detection system 130. In some embodiments, various SEP determination techniques are used (e.g., time domain SEP determination algorithms/classifiers), as disclosed herein.

In some embodiments, based on the SEP determination(s), the EEG control system 110 sends corresponding control signal(s) to the device 150 (e.g., based on associated SEPs). In some embodiments, the EEG detection system 130 sends raw EEG signal data, or in some embodiments processed EEG signal data (e.g., to filter out noise), to the EEG control system 110.

Figure 2:
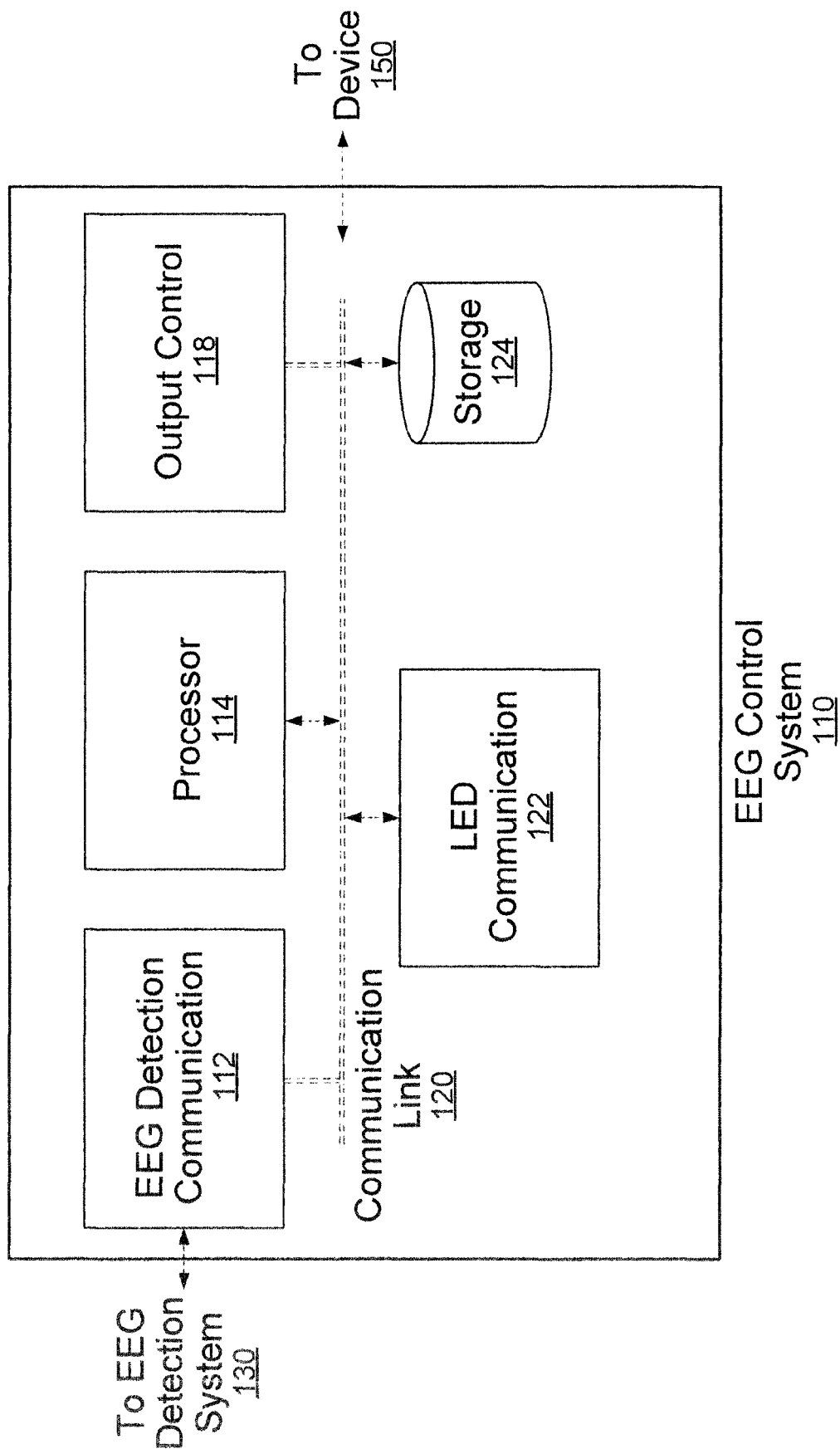
FIG. 2 is a functional diagram illustrating an EEG control system in accordance with some embodiments.

FIG. 2 is a functional diagram illustrating an EEG control system in accordance with some embodiments. As shown, the EEG control system 130 includes an EEG detection communication component 112 for communicating with the EEG detection system 130, a processor 114 for performing an SEP determination algorithm for EEG signals detected by EEG detection system 130, an output control 118 for communicating with the device 150, LED communication 122 for communicating with one or more LEDs (e.g., a flashing LED lights system), and a data storage 124 (e.g., for storing received EEG signal samples and associated timing data, such as for the flashing LED lights), and a communication link 120.

In some embodiments, a programmed computer is in communication with the EEG control system 110, and the EEG control system 110 also includes an EEG data to computer component for sending detected EEG signal samples to the computer. In this example, the computer includes a processor configured to perform an SEP determination algorithm for EEG signals detected by EEG detection system 130, and the computer can then provide the results of the analysis to the EEG control system for controlling the device (e.g., based on associated SEPs). In some embodiments, the computer includes a processor configured to perform an SEP determination algorithm for EEG signals detected by EEG detection system 130, and the computer sends corresponding control signal(s) to the device based on the results of the analysis of the EEG signal samples. In some embodiments, all or just a portion of the analysis of the EEG signal samples is performed by the programmed computer. In some embodiments, all or just a portion of the analysis of the EEG signal samples is performed in an EEG detection system (e.g., an ASIC integrated with or in communication with EEG sensors).

Figure 3:
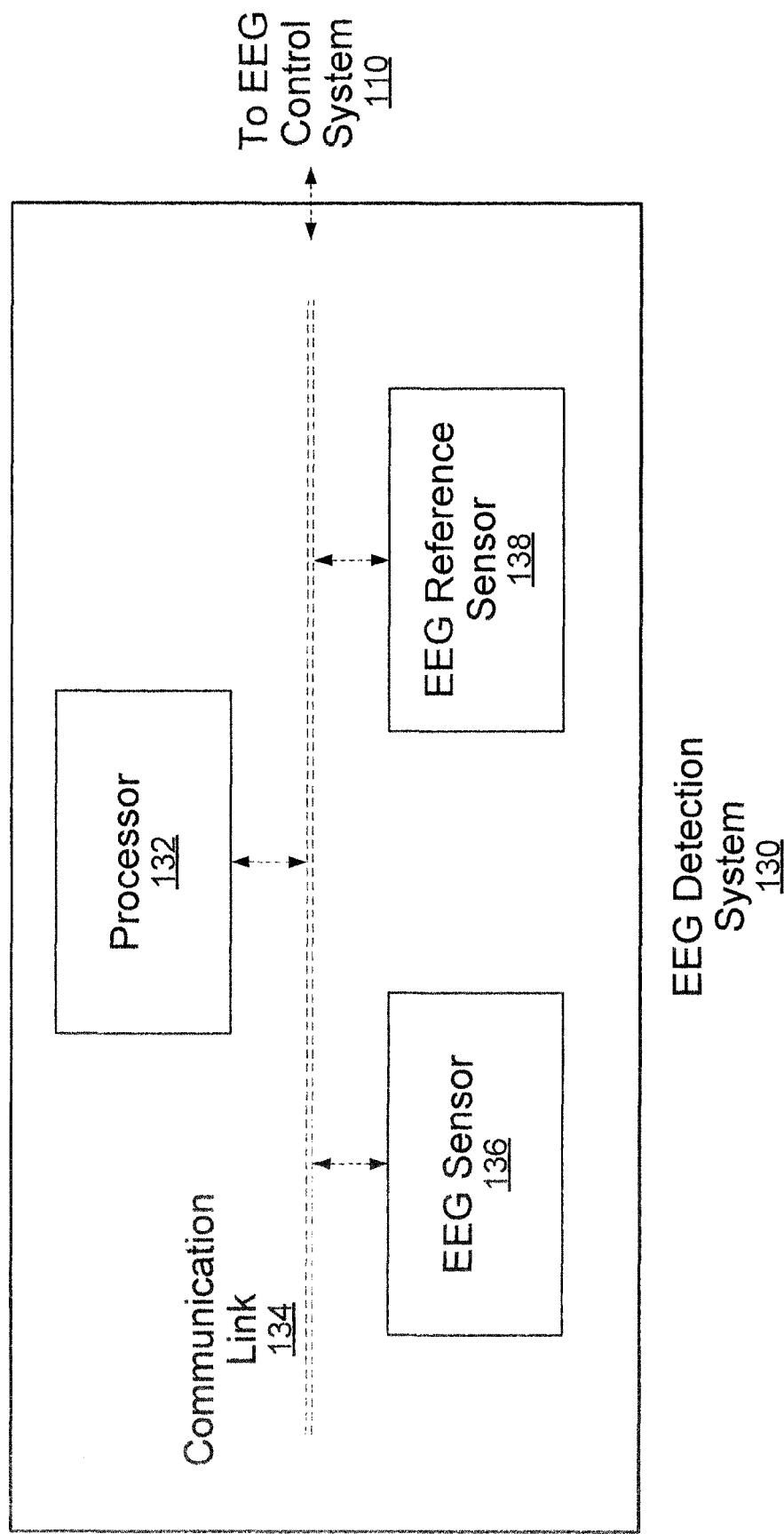
FIG. 3 is a functional diagram illustrating an EEG detection system in accordance with some embodiments.

FIG. 3 is a functional diagram illustrating an EEG detection system in accordance with some embodiments. As shown, the EEG detection system 130 includes a processor 132 (e.g., an FPGA or ASIC), active EEG sensor 136, and a reference EEG sensor 138, and a communication link 134. The measured EEG signals are provided to the EEG control system 110. In some embodiments, a continuous measure of EEG signal samples are detected and provided to the EEG control system 110.

Figure 4:
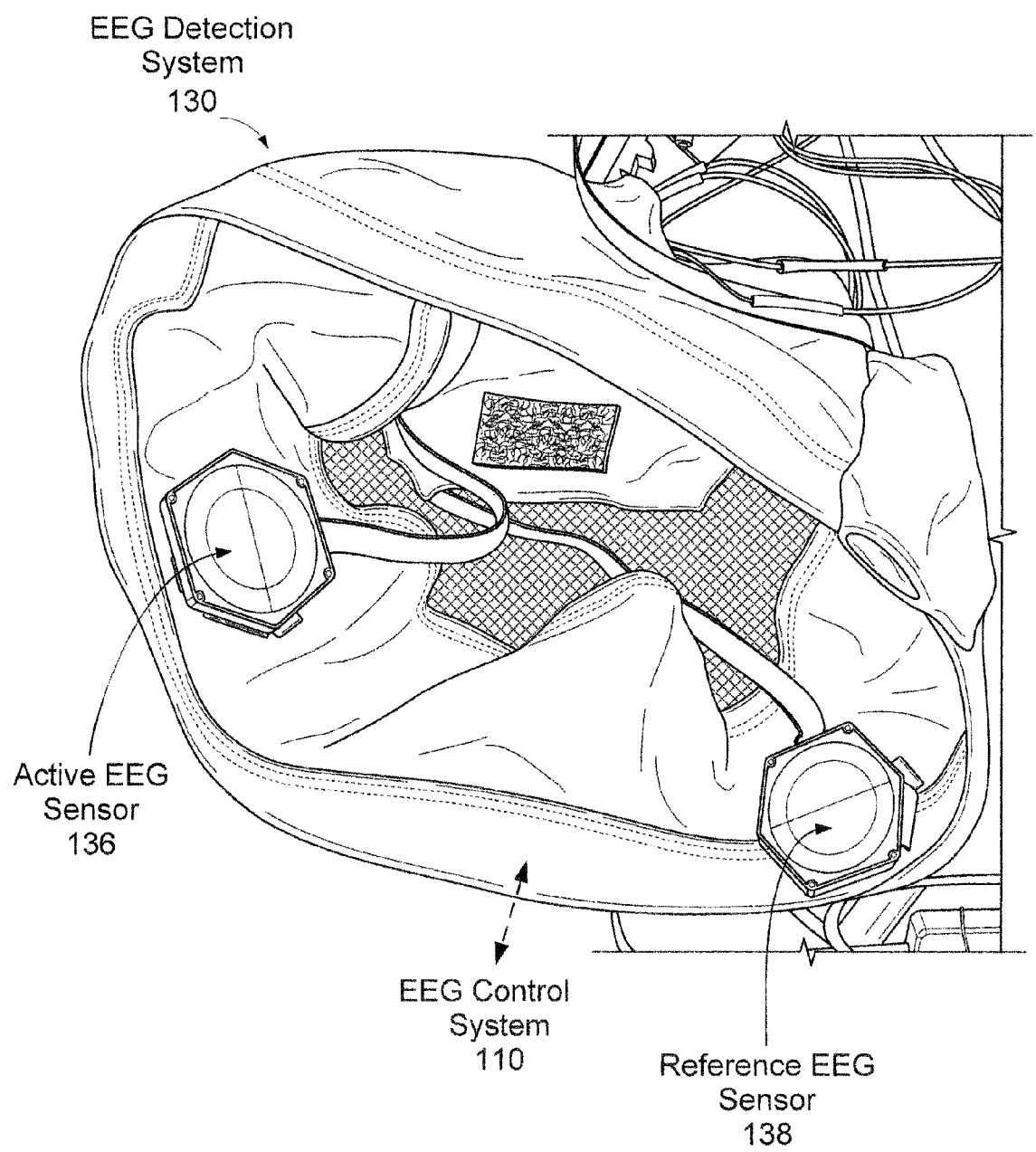
FIG. 4 illustrates an EEG detection system including an EEG sensor and reference EEG sensor mounted inside a hat in accordance with some embodiments.

FIG. 4 illustrates an EEG detection system including an EEG sensor and reference EEG sensor mounted inside a hat in accordance with some embodiments. As shown, the EEG detection system 130 is a hat to be worn by the user that includes the EEG sensor 136 and the reference EEG sensor 138 inside the hat. The EEG sensor 136 and the reference EEG sensor 138 are connected via a wired line communication (e.g., serial communication link) to the EEG control system 110. In some embodiments, the EEG sensor 136 is located inside the hat to be on the occipital region of the user's head (e.g., for visual event related EEG signal detection) when the hat is worn by the user, and the reference EEG sensor 138 is located in another location on the user's head (e.g., on the forehead, a side of the user's head above an ear, or on the back of the user's head in a location different than the location of the active EEG sensor). In some embodiments, the EEG sensor(s) are located in different locations based on the type of stimulus events to be detected as will be appreciated by those of ordinary skill in the art. In some embodiments, the EEG sensor 136 and reference EEG sensor 138 are non-contact EEG sensors. In some embodiments, the EEG detection system includes more than one EEG sensor 136. In some embodiments, the EEG detection system 130 is in the form of a headset, audio headset, an automobile seat headrest, or any other form of apparatus or module that can be used by the user to securely locate the EEG sensor(s) 136 and the reference EEG sensor 138 on appropriate locations of the user's head for EEG signal detection. In some embodiments, the EEG detection system 130 (e.g., a hat/cap, as shown) includes a grounded ear clip to reduce the amount of noise.

Figure 5B:
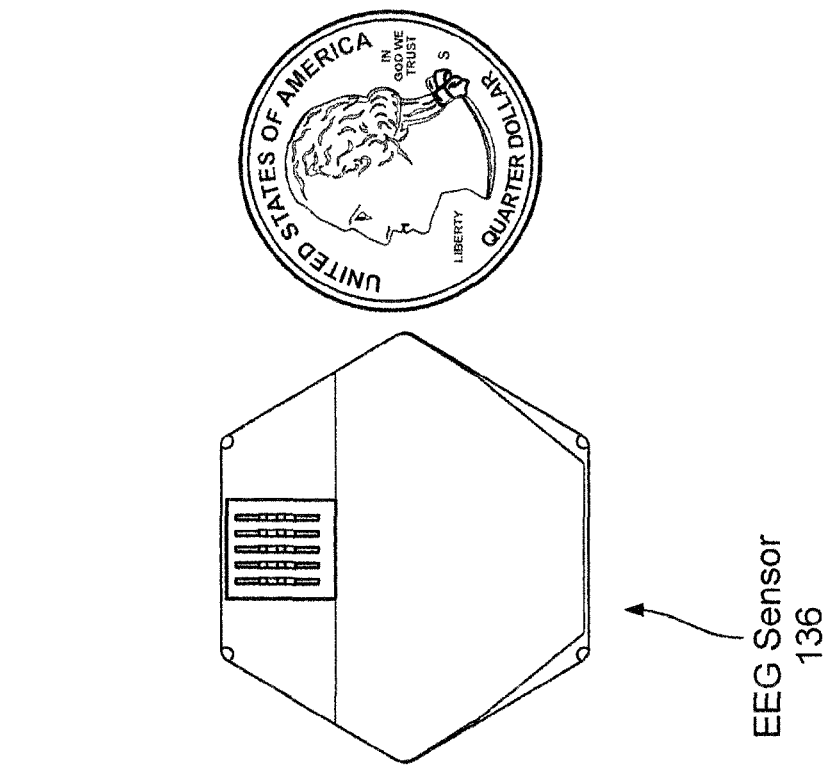
FIGS. 5A-5B illustrate EEG sensors in accordance with some embodiments.
Figure 5A:
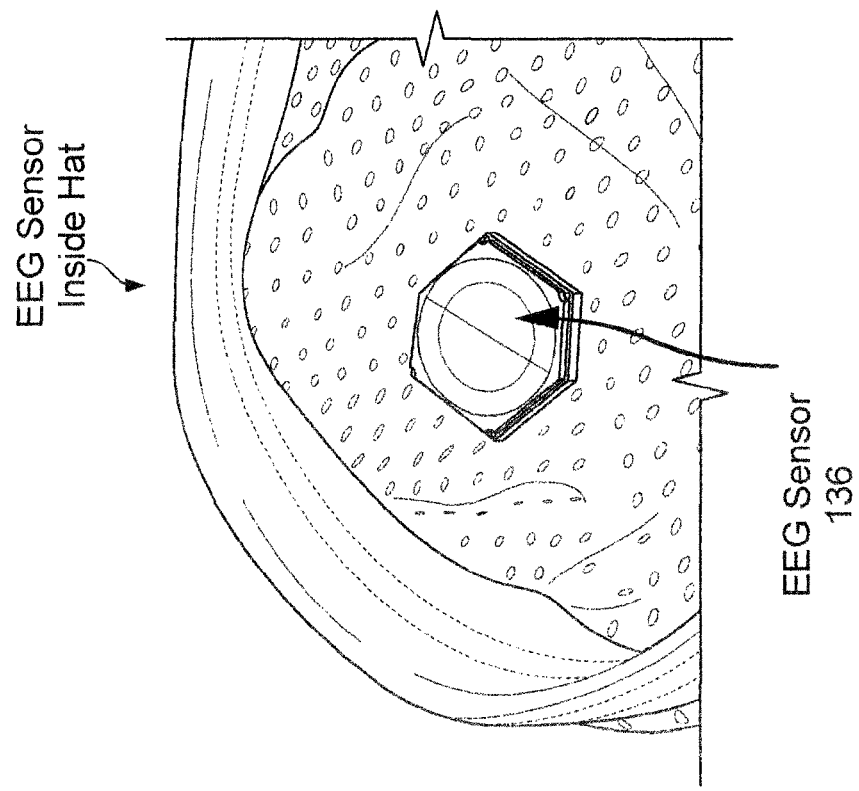

FIGS. 5A-5B illustrate EEG sensors in accordance with some embodiments. As shown in FIG. 5A, the EEG sensor 136 is mounted on the inside of the EEG signal detection hat. As shown in FIG. 5B, a top-side of the EEG sensor 136 is illustrated, in which the illustrated EEG sensor 136 is a non-contact electrode that is approximately the size of a U.S. quarter coin. The EEG sensor 136 is integrated into a printed circuit board (PCB) with analog front-end circuitry that amplifies the EEG signal and filters out noise. The EEG sensor 136 includes a metal shield, which protects, for example, the sensitive signal from external noise. In some embodiments, the circuitry for the EEG sensor 136 is integrated into an ASIC.

Figure 6:
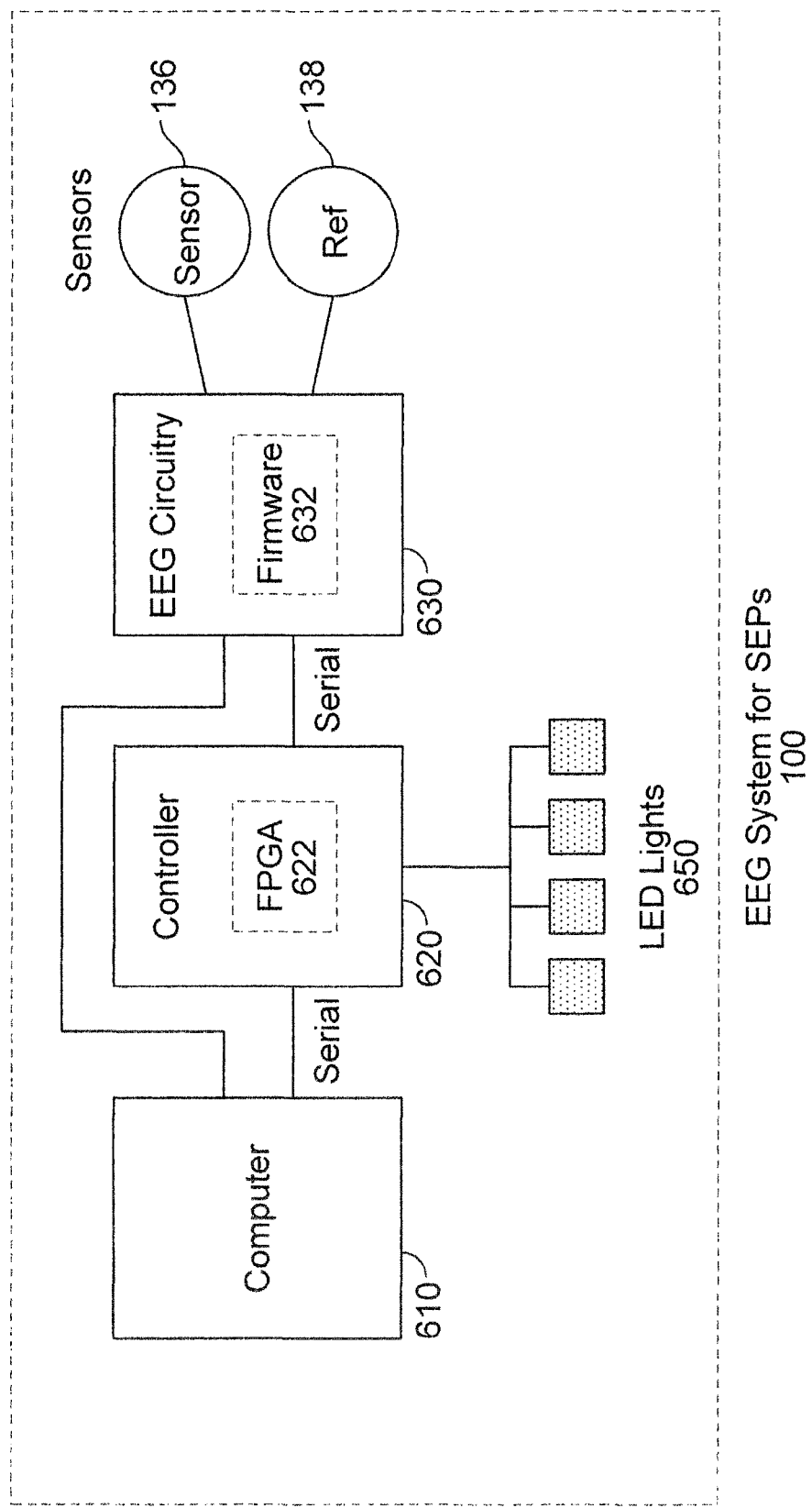
FIG. 6 is another block diagram illustrating an EEG system for SEPs in accordance with some embodiments.

FIG. 6 is another block diagram illustrating an EEG system for SEPs in accordance with some embodiments. As shown, the EEG system for SEPs 100 includes a computer 610 configured (e.g., programmed) to perform an SEP determination algorithm for detected EEG signals, a controller 620 for controlling LED (flashing) lights system 650 (e.g., controlling the timing of onsets and offsets of light flashes and which lights flash in which patterns), and EEG circuitry 630 for receiving (and in some embodiments, processing) detected EEG signals from the EEG sensor 136 and the reference EEG sensor 138. As shown, four LED lights are provided in the LED lights system 650. In some embodiments, one or more LED lights are provided.

The controller 620 also includes an FPGA 622 (or, in some embodiments, any other form of a processor or software executed on a processor, such as an ASIC or programmed processor). In some embodiments, the controller 620 controls the LED lights 650 and also communicates with the computer 610 and the EEG circuitry 630. In some embodiments, the controller 620 controls the flashing lights and receives EEG signal (sample) data from the EEG circuitry 630. In some embodiments, the controller also combines the received EEG signal data and light timing data (e.g., for the flashing onsets/offsets of the LED lights system 650) into a serial stream that is sent to the computer 610 for further analysis and processing (e.g., using a real-time SEP determination algorithm). In some embodiments, the controller 620 also sends control signals to a controlled device (e.g., the device 150).

The EEG circuitry 630 includes firmware 632 (or, in some embodiments, any other form of a processor or software executed on a processor, such as an ASIC or FPGA or programmed processor). The controller is in serial communication with the computer 610 and the EEG circuitry 630, as shown. In some embodiments, the EEG circuitry 630 is also directly connected to, as shown via a direct serial connection (or, in some embodiments, in direct communication, wired or wireless) with the computer 610. In some embodiments, one or more of these connections are wireless.

Figure 7:
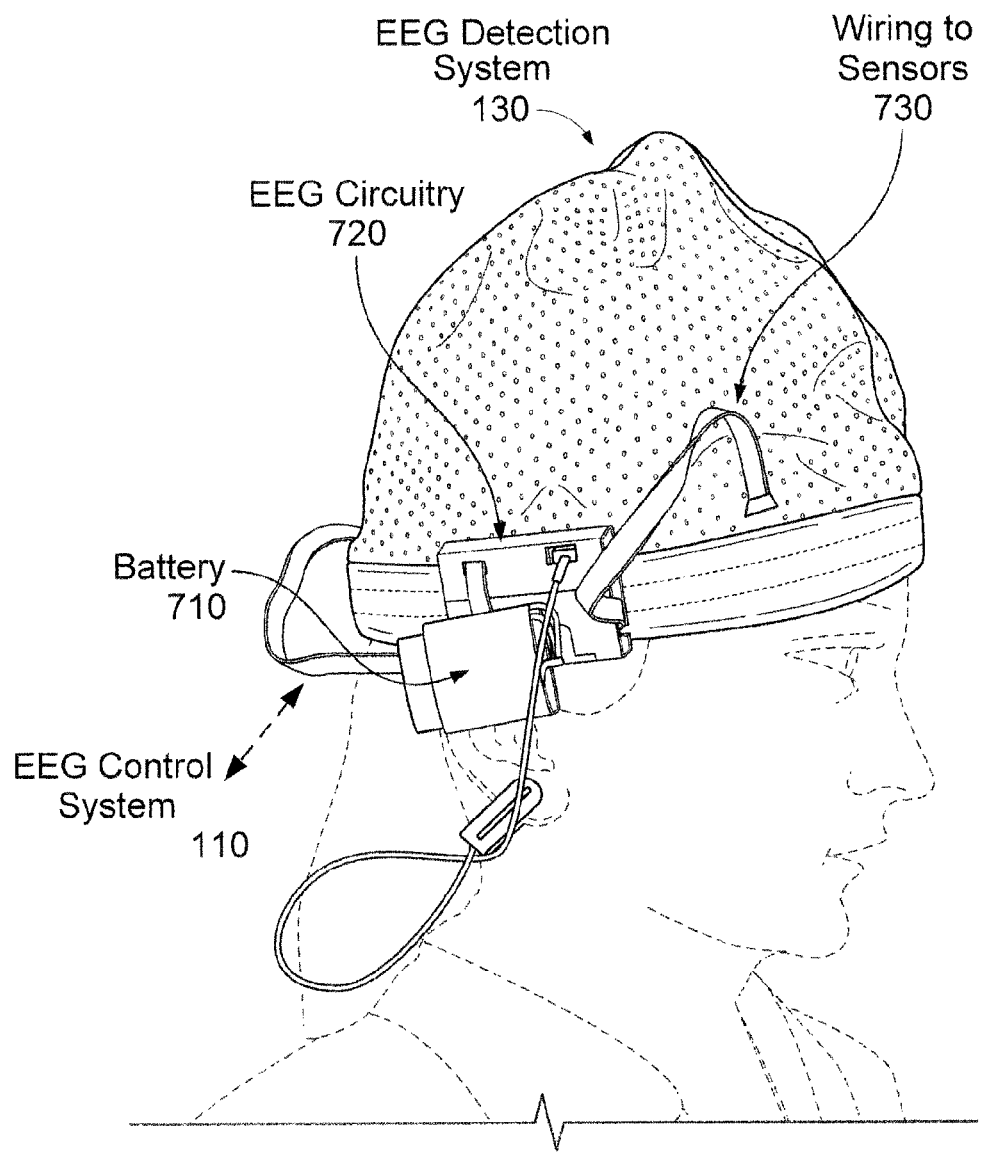
FIG. 7 illustrates an EEG detection system with non-contact EEG sensors in accordance with some embodiments.

FIG. 7 illustrates an EEG detection system with non-contact EEG sensors in accordance with some embodiments. As shown, the EEG detection system 130 is in the form of a hat or cap worn by the user, which includes a battery 710 (e.g., a rechargeable lithium ion battery), EEG circuitry 720, and wiring to the EEG sensors 730 (the non-contact EEG sensors are mounted inside of the hat and, thus, not visible in this depiction of the hat being worn by the user). In some embodiments, the EEG detection system 130 is in wireless (e.g., Bluetooth or another wireless protocol) with other apparatus/devices, such as the EEG control system 110. In some embodiments, the battery 710, EEG circuitry 720, and wiring to the EEG sensors 730 are more tightly integrated into the hat/cap and/or other head wear apparatus (as similarly discussed above), and, in some embodiments, generally not visible when worn by the user. As will be appreciated, various other designs and head wear apparatus can be used to provide the EEG detection system 130 disclosed herein.

Figure 8B:
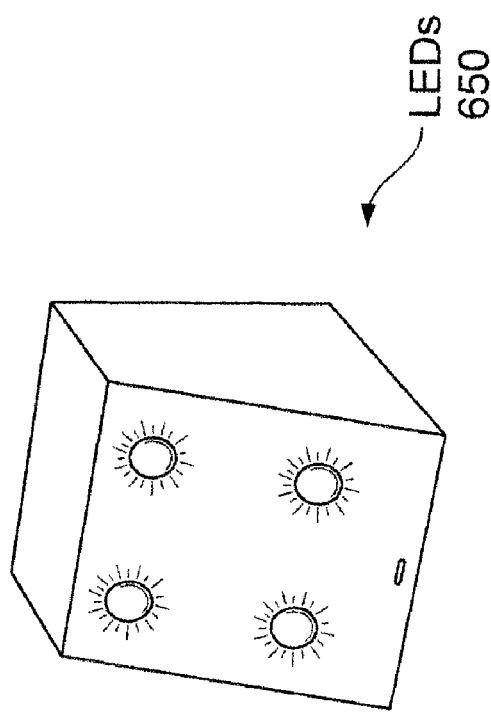
FIGS. 8A-8B illustrate LED lights for an EEG system for SEPs in accordance with some embodiments.
Figure 8A:
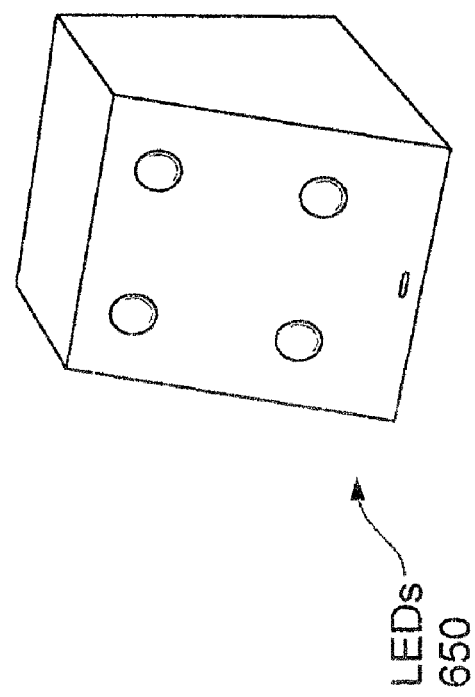

FIGS. 8A-8B illustrate LED lights for an EEG system for SEPs in accordance with some embodiments. As shown, FIG. 8A illustrates the LED lights 650 in which all four LED lights are turned off (e.g., not flashed on). As shown, FIG. 8B illustrates the LED lights 650 in which all four LED lights are turned on (e.g., flashed on). As shown, the LED lights 650 are mounted in a box shaped apparatus, which, for example, can flash in patterns that represent commands to a user. In some embodiments, each of the four separate LED lights of the LED lights system 650 can flash on/off independently. In some embodiments, the LED lights of the LED lights system 650 flash at distinct fixed frequencies. In some embodiments, the LED lights of the LED lights system 650 flash at variable frequencies in a fixed pattern. In some embodiments, each of the four LED lights flashes at a different frequency. In some embodiments, the frequencies of each of the LED lights are separated by 1 or 2 Hz (e.g., the four LED lights can be set at the following frequencies: 9 Hz, 10 Hz, 11 Hz, and 12 Hz, or other frequencies, such as in the range of 8 Hz to 20 Hz or some other frequency range for which SEPs can effectively be detected). In some embodiments, fewer than four or more than four LEDs are included in the LED lights system 650. In some embodiments, the flashing pattern is controlled by the controller 620 (e.g., controlling the frequency of the flashing using an FPGA controller, such as a Xilinx FPGA chip that executes Verilog code).

Figure 9A:
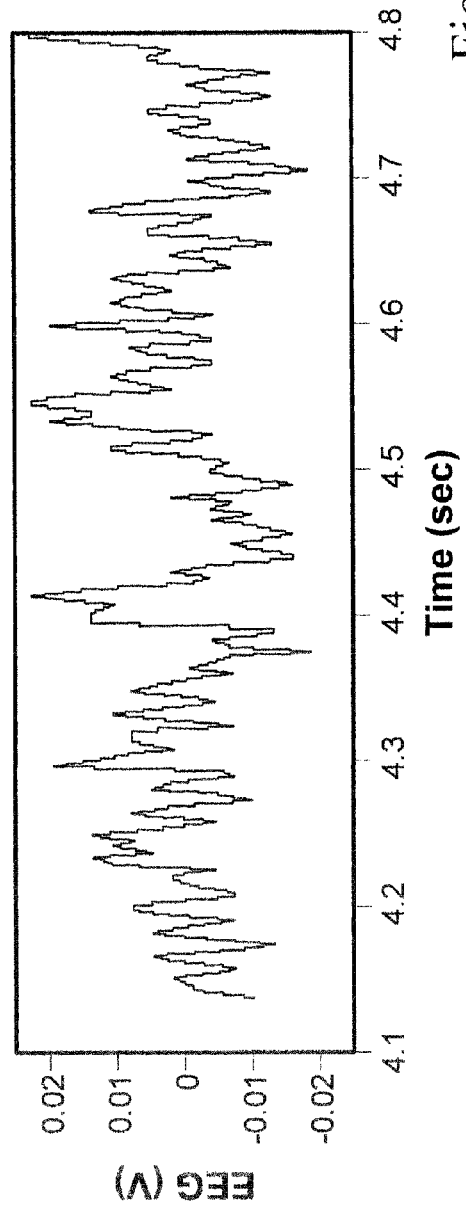
FIGS. 9A-9B are charts illustrating EEG data and light control signal data for an EEG system for SEPs in accordance with some embodiments.
Figure 9B:
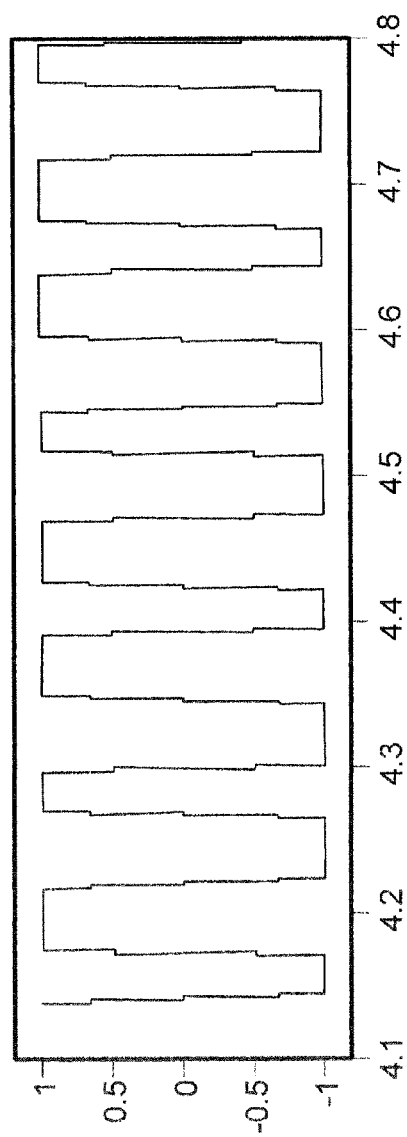

FIGS. 9A-9B are charts illustrating EEG data and light control signal data for an EEG system for SEPs in accordance with some embodiments. FIG. 9A illustrates measured EEG signals (in Volts (V)) relative to time (in seconds). FIG. 9B illustrates the light input signal (in Hertz (Hz)) (e.g., flashing light events) relative to time (in seconds). As shown, the light input signal is a square wave of a fixed frequency.

Figure 10:
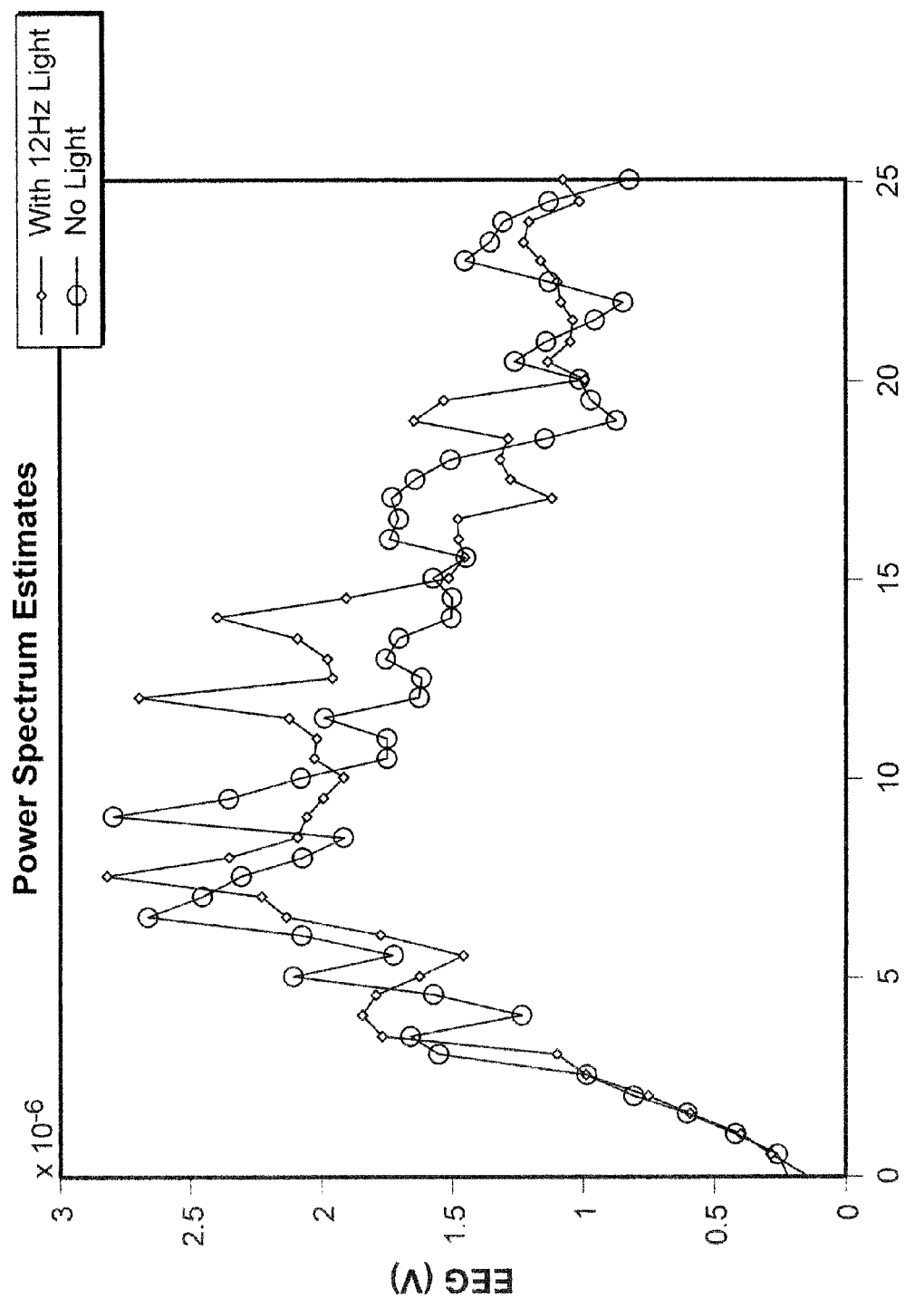
FIG. 10 is a power spectrum chart for sample EEG data.

FIG. 10 is a power spectrum chart for sample EEG data. In particular, FIG. 10 illustrates measured EEG signals (in V) relative to frequency (in Hz), in which there are two measurements depicted, a first measured EEG signal for which no light events are present, and a second measured signal for which 12 Hz light events occurred and the user was looking at a light that flashed on and off at a fixed frequency of 12 Hz. As illustrated in this example shown in FIG. 10 and as discussed above, it is difficult to determine if the increased power at 12 Hz is due to looking at a 12 Hz light, or if it is irrelevant noise.

Figure 11:
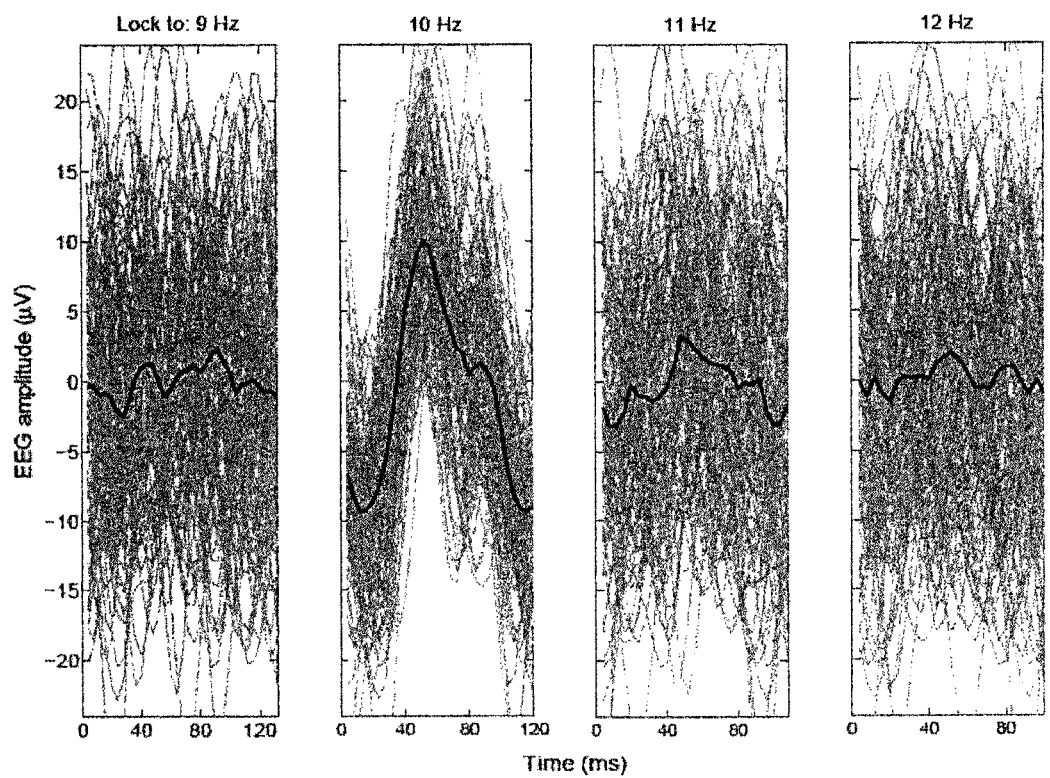
FIG. 11 is a chart illustrating EEG segments and averaged EEG following light onsets for an EEG system for SEPs in accordance with some embodiments.

FIG. 11 is a chart illustrating EEG segments and averaged EEG following the light onsets for an EEG system for SEPs in accordance with some embodiments. The user was attending a light flashing at 10 Hz, and each of the four panels shows EEG segments as they are locked to onsets of one of the four lights (flashing at 9, 10, 11 and 12 Hz, respectively). The black curves show the average of the EEG segments. When EEG segments are locked to the repeated onsets of the stimulus being attended, there exists significantly higher inter-segment correlation. The average of the correlation coefficients between all pairs of EEG segments can be one way to measure this correlated activity. Also as shown, the flash-locked average signal provides a signal shape that can be recognized to detect that the light is being attended (e.g., observed by the user), such that an SEP is effectively detected (e.g., using a threshold comparison and/or a signature signal comparison, as discussed herein).

Figure 12:
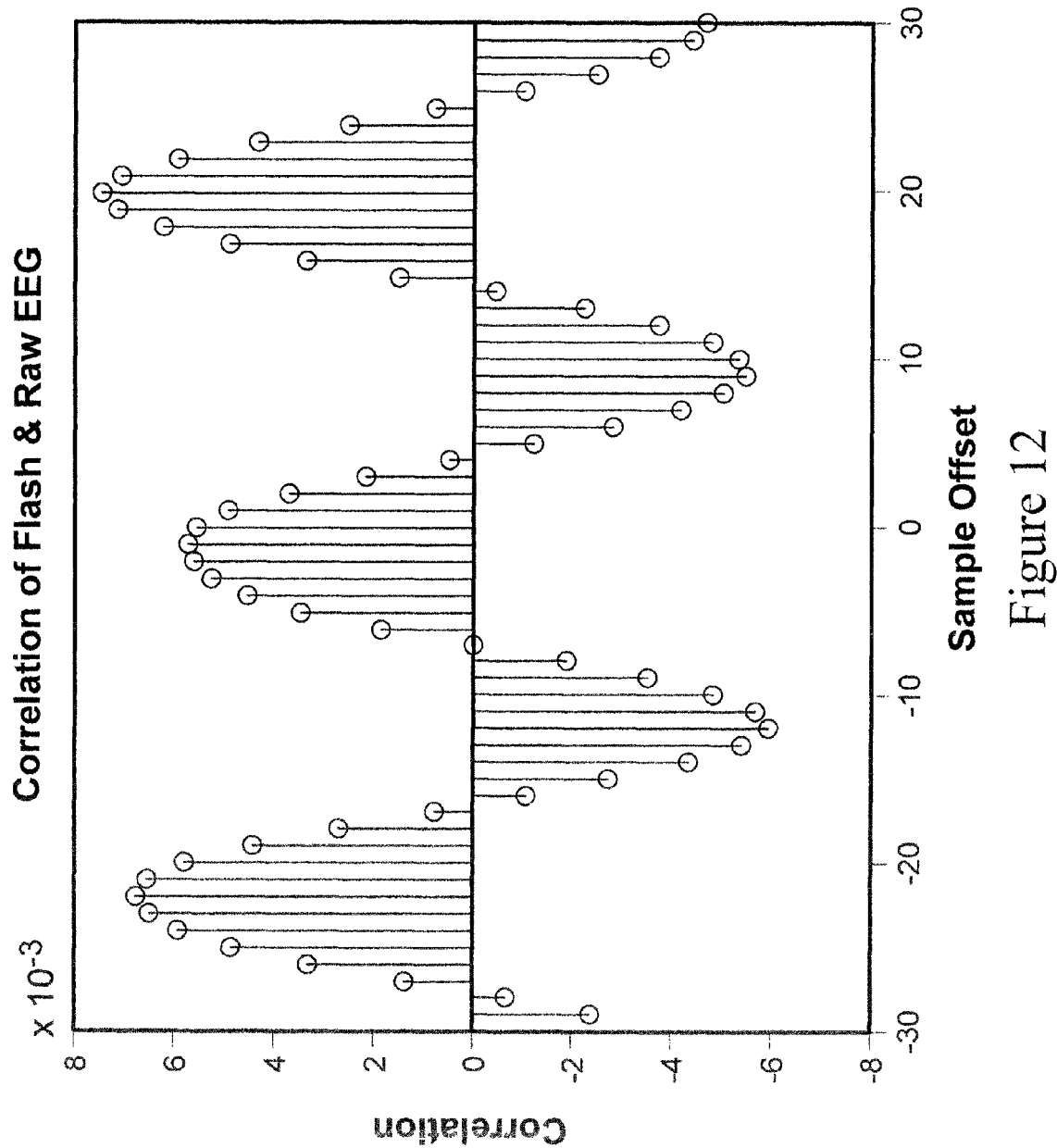
FIG. 12 is a chart illustrating a correlation of light flash and raw EEG data for an EEG system for SEPs in accordance with some embodiments.

FIG. 12 is a chart illustrating a correlation of flash and raw EEG data for an EEG system for SEPs in accordance with some embodiments. In particular, FIG. 12 illustrates a correlation analysis between averaged EEG signals (e.g., flash-locked average signals) and flashing light events (e.g., light flashes). At each discrete point in time, the measured EEG signals and the measured light signals are multiplied together. All of these results are averaged together to form a correlation number. In some embodiments, the analysis is repeated using time offsets between the EEG data and the light signal data (e.g., 30 ms). The result is a characteristic shape that can be used to determine that the light is being attended (e.g., observed by the user), such that an SEP is effectively detected.

Figure 13:
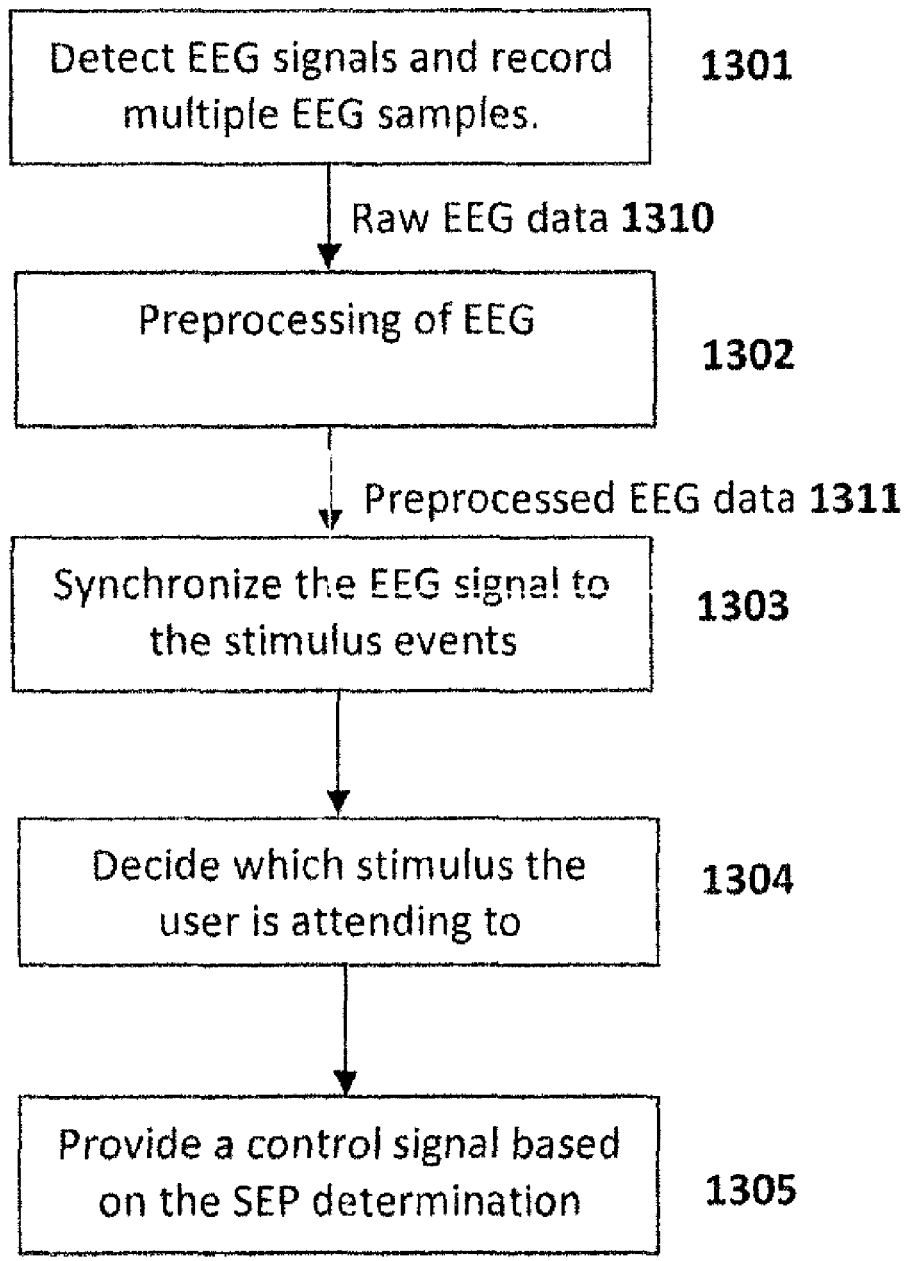
FIG. 13 is a flow chart for techniques for SEP signal detection or classification in accordance with some embodiments.
Figure 14:
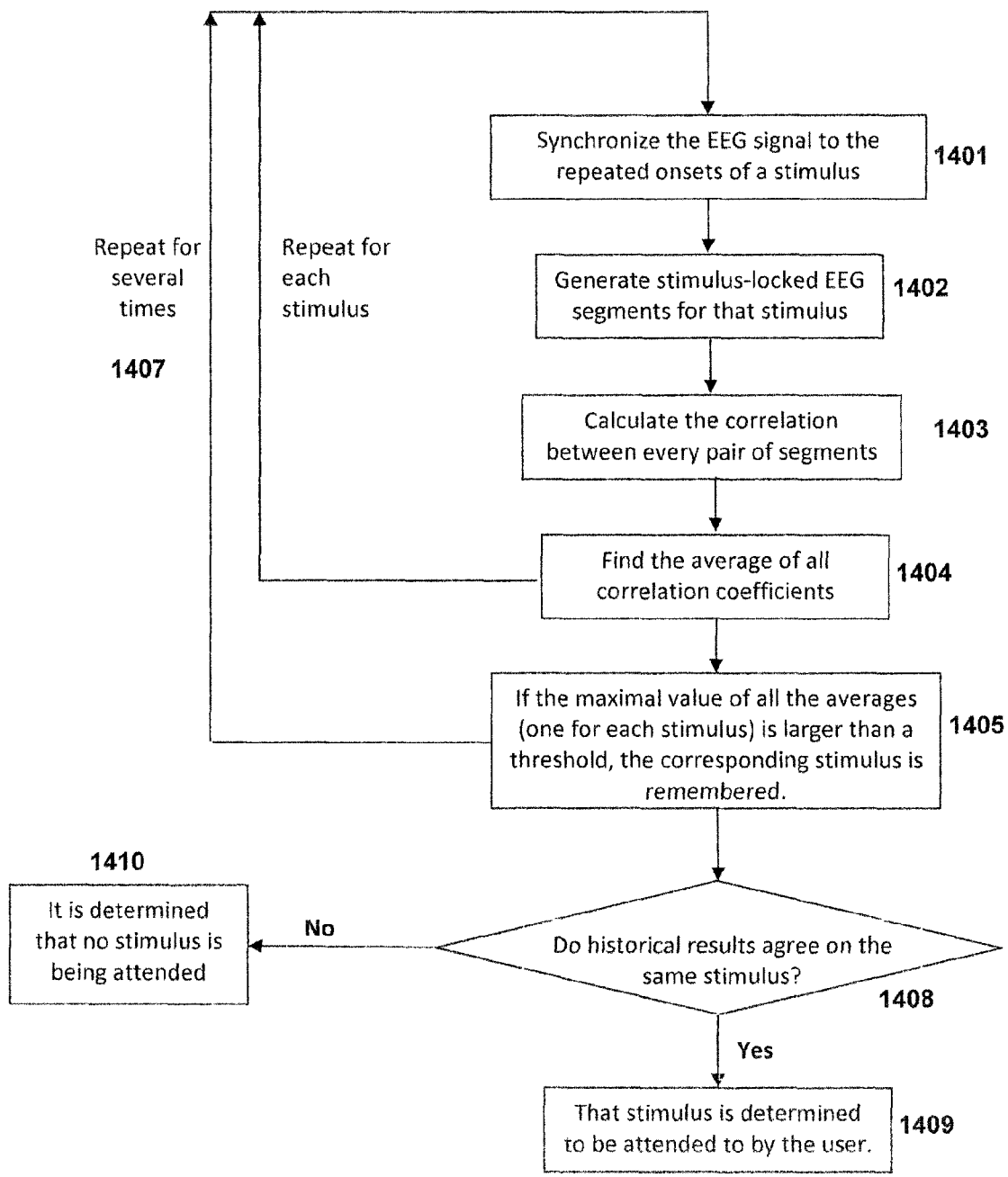
FIG. 14 is a flow chart for an example algorithm for SEP in accordance with some embodiments.

FIG. 13 is a flow chart of a technique for SEP signal detection or classification in accordance with some embodiments. In some embodiments, the algorithm is running iteratively and continuously in real-time. In some embodiments, the algorithm analyzes data offline (e.g., after all data are collected). At 1301, multiple EEG signal samples are detected and recorded. At 1302, in some embodiments, one or more preprocessing techniques, such as filtering (to remove DC drifts and/or high frequency noise), re-sampling (to change the sampling frequency of the raw EEG data 1310, such as down sampling, up sampling, interpolation, etc.) and/or artifact/movement removal (to remove artifacts caused by eye blinks, muscle noise, movement, EKG, etc.) can be applied to prepare the EEG for further data analysis. At 1303, the EEG signal (using the preprocessed EEG data 1311) is synchronized to the stimulus events/status. At 1304, whether the EEG signal samples are evoked in response to a pattern of stimulus events (e.g., an SEP determination, such as in response to a visual event) is determined in a variety of ways, such as a stimulus-locked average method or an inter-segment correlation method. A detailed description of an inter-segment correlation method is illustrated in FIG. 14. At 1305, a control signal is provided based on the SEP determination.

FIG. 14 is a flow chart illustrating one technique for determining whether the user is attending to a stimulus or which stimulus the user is attending to in accordance with some embodiments. At 1401, the EEG signal is synchronized to the repeated onsets of a stimulus. At 1402, stimulus-locked EEG segments are generated for that stimulus. In some embodiments, the length of the segments is shorter/longer than the time interval between two stimulus onsets. At 1403, the correlation coefficient between every pair of the segments is computed. In some embodiments, the correlation coefficient can be computed only between some pairs of the segments. In some embodiments, other values that measure the mutual relationship between these segments, such as mutual information, are computed. At 1404, the average of the correlation coefficients is computed. In some embodiments, the median value, instead of the average, of the correlation coefficients can be computed. At 1406, steps 1401 to 1404 are repeated for each stimulus. At 1405, if the maximal value among all averages (one for each stimulus) is larger than a threshold, the corresponding stimulus is remembered. In some embodiments, the system is trained based on testing with a particular user, and the threshold values (or, in some embodiments, signal signatures) are generated based on the training. At 1407, steps 1401 to 1405 are repeated for a few times. At 1408, if the historical results agree on a same stimulus, the corresponding stimulus is determined to be attended by the user at 1409; otherwise, it is determined that no stimulus is being attended at 1410.

Figure 15:
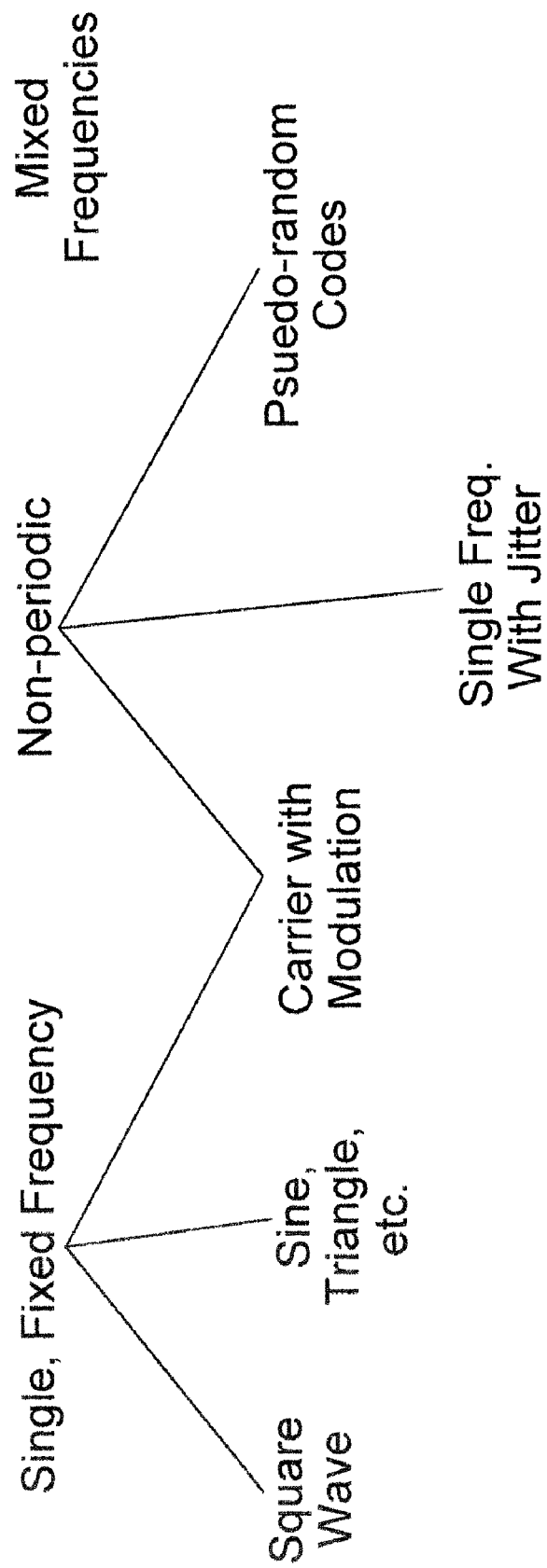
FIG. 15 is a diagram illustrating different stimulus types in accordance with some embodiments.

FIG. 15 is a diagram illustrating different stimulus frequency types in accordance with some embodiments. As shown, a stimulus frequency for the light input signal can be a single, fixed frequency, such as a square wave, a sign or triangle wave, or a carrier with modulation. In some embodiments, a mixed frequency stimulus is used, in which a mixed frequency stimulus is, for example, a combination of two or more fixed frequencies added together. In some embodiments, various other types of non-periodic signals are used and are matched with time domain analysis. For example, a carrier wave with modulation would be similar to an FM radio signal with a large sine-wave component at a fixed frequency combined with a different smaller signal. As another example, a single-frequency stimulus can be adjusted by adding some variation in the frequency. As will be appreciated, there are also many ways to construct pseudo-random codes, such as CDMA codes used in cell phone networks.

Figure 16:
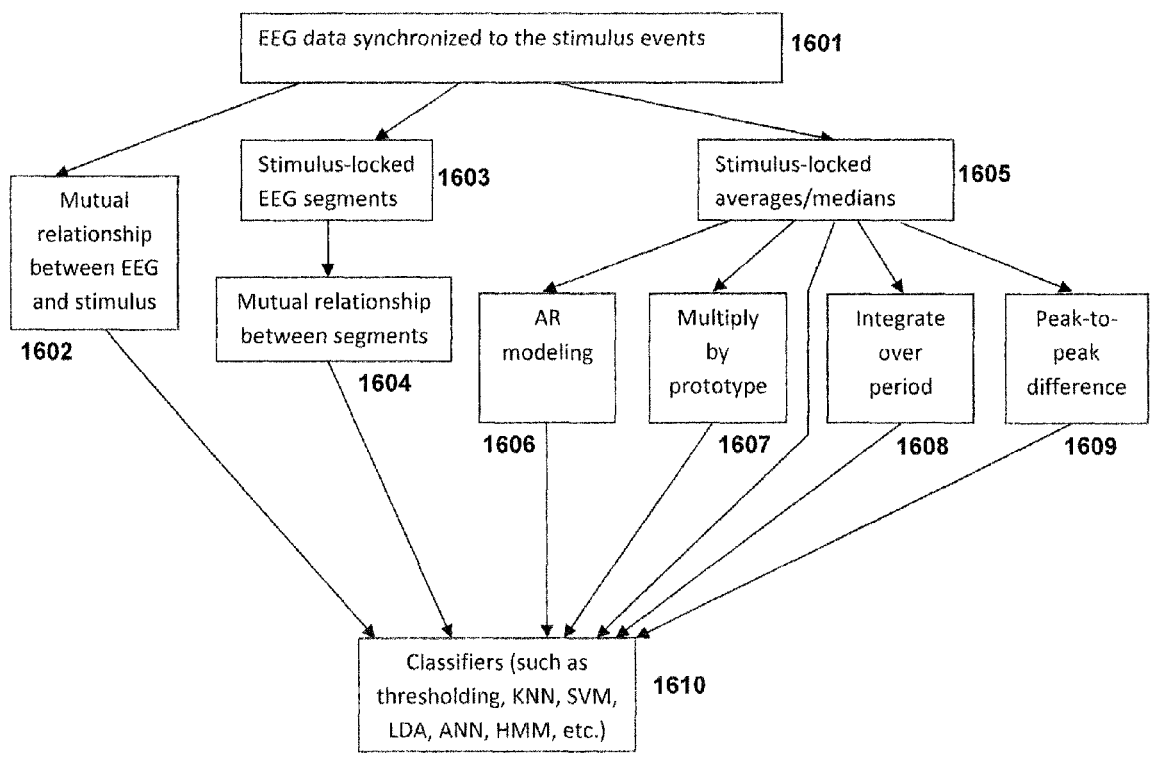
FIG. 16 is a diagram illustrating time domain algorithms in accordance with some embodiments.

FIG. 16 is a diagram illustrating time domain algorithms in accordance with some embodiments. In some embodiments, time domain classifier techniques use the EEG signal without a conversion to the frequency domain. For example, at 1601, the EEG is synchronized to the stimulus events/status. At 1602, one approach that can be used is to compute the mutual relationship, such as correlation or mutual information, between EEG and stimulus. If the user is attending to that stimulus, the output will have a relatively larger amplitude, compared with other stimuli. The mutual relationship can also be computed between the stimulus and a delayed version of the EEG (e.g., using an appropriate offset, such as 30 ms to 50 ms). At some delay, the mutual relationship will typically be strong for a stimulus that is being attended. At 1603, some embodiments of the time-domain algorithm generate stimulus-locked EEG segments. At 1604, the mutual relationship between these segments is computed in some embodiments. At 1605, stimulus-locked average is computed for each stimulus in some embodiments. In some embodiments, other stimulus-locked signals, such as stimulus-locked median/ sum or variance, may be computed for each stimulus. At 1606, an auto-regression model of EEG can be constructed when a user is known to be looking at the stimulus, and the coefficients of that auto-regression model can be used as the data elements for further classification. At 1607, a prototype of an ideal average (e.g., when a light is being attended) can be constructed and multiplied by the actual average. A high value result will indicate an attended light. The prototype can be constructed in a variety of ways, including computing EEG averages when a user is known to be looking at the light. At 1608, the absolute value of the averaged EEG is integrated over some time period. At 1609, the peak-to-peak difference in the averaged EEG is computed. At 1610, classification methods, such as thresholding, linear discrimination analysis (LDA), K-nearest neighbor (KNN), support vector machine (SVM), artificial neural network (ANN), hidden Markov model (HMM), can be used to further decide whether the user is attending to a specific stimulus.

FIG. 17 is a chart illustrating an example of four stimulus-locked averages in accordance with some embodiments. One of the averages has developed a characteristic shape, and the other averages are relatively flat.

FIG. 18 is a chart illustrating an example for generating a stimulus-locked signal in accordance with some embodiments. As shown in FIG. 18, an EEG signal 1801 from a user attending to a stimulus and a signal 1802 that is used to control the stimulus are both measured. Segments of the EEG signal of a fixed length (e.g., 500 ms) that follow the stimulus onsets are first recorded. In some embodiments, the correlation 1803 between EEG and stimulus is computed and used for further classification. In some embodiments, the EEG segments are extracted such that the first data point in each segment is the first EEG sample recorded after a stimulus onset, the second data point in each segment is the second EEG sample recorded after a stimulus onset, and so forth. These segments can have the same length as the time interval between two stimulus onsets or can be longer or shorter. At 1804, the segments are averaged together such that the first EEG data points following light onsets are averaged together, then all the second data points that follow light onsets are averaged together, then the third data points that follow light onsets are averaged together, and so forth. The result provides an average waveform. In some embodiments, the measured EEG signals include involuntary EEG signal responses. In some embodiments, the measured EEG signals also include voluntary EEG signal responses, such as intensity or focus related EEG signal responses (e.g., the strength of the EEG signal can be altered by the way in which (such as a periphery versus a direct focus) or the intensity with which a user looks at a flashing light(s)). At 1805, the correlation between every pair of these segments can be computed. In some embodiments, only a subset of these segments (such as the second, the forth, the sixth . . . segments) are used. In some embodiments, only a part of these segments (such as from 100 ms after the stimulus onset) are used.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method for sensory-evoked potential signal classification, comprising:

generating a pattern of stimulus characterized by a frequency that updates randomly;

determining in real-time the frequency of the pattern of stimulus, the determined frequency of the pattern of stimulus being the current frequency of the pattern of stimulus;

receiving a plurality of electroencephalography signal samples from a current user evoked in response to the pattern of stimulus;

synchronizing the plurality of electroencephalography signal samples in time domain without conversion to a frequency domain to the pattern of stimulus in time domain;

generating a stimulus-locked electroencephalography signal sample using a processor; and performing a determination using a time domain classifier in real-time of whether the plurality of electroencephalography signal samples are evoked in response to the pattern of stimulus using the processor, wherein the determination of whether the plurality of electroencephalography signal samples are evoked in response to the pattern of stimulus being performed dynamically or adaptively in real-time in a manner such that the current user's electroencephalography pattern determined in real-time is used, the current user's electroencephalography response pattern determined before the current user's current electroencephalography response pattern is not used, the frequency of the pattern of stimulus determined in real-time is used, and a frequency of the pattern of stimulus determined before the current determined frequency of the pattern of stimulus is not used in the determination of whether the plurality of electroencephalography signal samples are evoked in response to the pattern of stimulus; and wherein the sensory-evoked potential signal classification is computed by calculating a mutual relationship between pairs of segments for the stimulus-locked electroencephalography signal sample, determining a statistical measure of the mutual relationship for each stimulus, and determining if a stimulus is being attended to by the current user according to the statistical measure of the mutual relationship for each stimulus user the time domain classifier.

2. The method recited in claim 1, wherein sensory-evoked potential signal classification is performed by synchronizing electroencephalography signal samples to repeated presentation of sensory stimuli in the time domain.

3. The method recited in claim 1, wherein sensory-evoked potential signal classification is performed by synchronizing electroencephalography signal samples to repeated presentation of sensory stimuli in the time domain, wherein the sensory-evoked potential signal classification includes visually evoked potentials.

4. The method recited in claim 1, further comprising: detecting a plurality of electroencephalography signals.

5. The method recited in claim 1, further comprising: recording the plurality of electroencephalography signal samples.

6. The method recited in claim 1, further comprising: synchronizing the plurality of electroencephalography signal samples to the pattern of stimulus.

7. The method recited in claim 1, further comprising: synchronizing each electroencephalography signal sample to an onset of the pattern of stimulus.

8. The method recited in claim 1, further comprising: determining which stimulus is attended to by a user.

9. The method recited in claim 1, further comprising: generating a control signal based on the sensory-evoked potential signal classification.

10. The method recited in claim 1, wherein the mutual relationship includes correlation, mutual information, or covariance.

11. The method recited in claim 1, wherein the statistical measure includes a mean, a median value, or a sum.

12. A method recited in claim 1, further comprising receiving a signal that is used to control the pattern of stimulus.

13. A system for sensory-evoked potential signal classification, comprising:
a processor configured to:
generate a pattern of stimulus characterized by a frequency that updates randomly;
determine in real-time the frequency of the pattern of stimulus, the determined frequency of the pattern of stimulus being the current determined frequency of the pattern of stimulus;
receive a plurality of electroencephalography signal samples from a current user evoked in response to the pattern of stimulus;
synchronize the plurality of electroencephalography signal samples in time domain without conversion to a frequency domain to the pattern of stimulus in time domain;
generate a stimulus-locked electroencephalography signal sample; and
perform a determination using a time domain classifier in real-time of whether the plurality of electroencephalography signal samples are evoked in response to the pattern of stimulus, wherein the determination of whether the plurality of electroencephalography signal samples are evoked in response to the pattern of stimulus being performed dynamically or adaptively in real-time in a manner such that the current user's electroencephalography pattern determined in real-time is used, the current user's electroencephalography response pattern determined before the current user's current electroencephalography response pattern is not used, the frequency of the pattern of stimulus determined in real-time is used, and a frequency of the pattern of stimulus determined before the current determined frequency of the pattern of stimulus is not used in the determination of whether the plurality of electroencephalography signal samples are evoked in response to the pattern of stimulus; and wherein the sensory-evoked potential signal classification is computed by calculating a mutual relationship between pairs of segments for the stimulus-locked electroencephalography signal sample, determine a statistical measure of the mutual relationship for each stimulus, and determine if a stimulus is being attended to by the current user according to the statistical measure of the mutual relationship for each stimulus user the time domain classifier; and a memory coupled to the processor and configured to provide the processor with instructions.

14. The system recited in claim 13, wherein sensory-evoked potential signal classification is performed by synchronizing electroencephalography signal samples to repeated presentation of sensory stimuli in the time domain, wherein the sensory-evoked potential signal classification includes visually evoked potentials.

15. A computer program product for sensory-evoked potential signal classification, the computer program product being embodied in a non-transitory computer readable storage medium and comprising computer instructions for:
generating a pattern of stimulus characterized by a frequency that updates randomly;
determining the frequency of the pattern of stimulus determined in real-time, the determined frequency of the pattern of stimulus being the current determined frequency of the pattern of stimulus;
receiving a plurality of electroencephalography signal samples from a current user evoked in response to the pattern of stimulus;
synchronizing the plurality of electroencephalography signal samples in time domain without conversion to a frequency domain to the pattern of stimulus in time domain;
generating a stimulus-locked electroencephalography signal sample using a processor; and
performing a determination using a time domain classifier in real-time of whether the plurality of electroencephalography signal samples are evoked in response to the pattern of stimulus using the processor,
wherein the determination of whether the plurality of electroencephalography signal samples are evoked in response to the pattern of stimulus being performed dynamically or adaptively in real-time in a manner such that the current user's electroencephalography pattern determined in real-time is used, the current user's electroencephalography response pattern determined before the current user's current electroencephalography response pattern is not used, the frequency of the pattern of stimulus determined in real-time is used, and a frequency of the pattern of stimulus determined before the current determined frequency of the pattern of stimulus is not used in the determination of whether the plurality of electroencephalography signal samples are evoked in response to the pattern of stimulus; and wherein the sensory-evoked potential signal classification is computed by calculating a mutual relationship between pairs of segments for the stimulus-locked electroencephalography signal sample, determining a statistical measure of the mutual relationship for each stimulus, and determining if a stimulus is being attended to by the current user according to the statistical measure of the mutual relationship for each stimulus user the time domain classifier.

16. The computer program product recited in claim 15, wherein sensory-evoked potential signal classification is performed by synchronizing electroencephalography signal samples to repeated presentation of sensory stimuli in the time domain, wherein the sensory-evoked potential signal classification includes visually evoked potentials.

* * * * *